(12) United States Patent
Pauker

(10) Patent No.: US 10,441,152 B2
(45) Date of Patent: Oct. 15, 2019

(54) TRACKING THE FUNDAMENTAL FREQUENCY OF A VOICE SIGNAL IN REAL TIME

(71) Applicant: Digital Endoscopy GmbH, Friedberg (DE)

(72) Inventor: Friedrich Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 390 days.

(21) Appl. No.: 15/113,034

(22) PCT Filed: Jan. 22, 2015

(86) PCT No.: PCT/EP2015/051245
§ 371 (c)(1),
(2) Date: Oct. 21, 2016

(87) PCT Pub. No.: WO2015/110525
PCT Pub. Date: Jul. 30, 2015

(65) Prior Publication Data
US 2017/0035285 A1    Feb. 9, 2017

(30) Foreign Application Priority Data
Jan. 24, 2014 (DE) .......... 10 2014 201 286

(51) Int. Cl.
*A61B 1/267* (2006.01)
*A61B 1/00* (2006.01)
(Continued)

(52) U.S. Cl.
CPC ........ *A61B 1/2673* (2013.01); *A61B 1/00006* (2013.01); *A61B 5/4803* (2013.01);
(Continued)

(58) Field of Classification Search
CPC . A61B 1/0052; A61B 1/00137; A61B 1/0057; A61B 1/0125; A61B 1/2673; A61B 5/4803
See application file for complete search history.

(56) References Cited

U.S. PATENT DOCUMENTS 3,549,806 A    12/1970  Wood
3,605,725 A     9/1971  Bentov
(Continued)

FOREIGN PATENT DOCUMENTS

CN    1286664 A    3/2001
CN    2762381 Y    3/2006
(Continued)

OTHER PUBLICATIONS

Search Report for Application CN 2015800056419 in 2 pages (English translation).
(Continued)

*Primary Examiner* — Patrick Fernandes
(74) *Attorney, Agent, or Firm* — Knobbe, Martens, Olson & Bear, LLP

(57) ABSTRACT

The invention relates to a method and an apparatus for tracking a fundamental frequency of a voice signal. A sampling device samples a voice signal of a test person for a predetermined period of time (S1), thus obtaining sampling data of the voice signal, forms a data packet from the sampling data (S2), and sends the data packet to a calculating device (S3). The calculating device receives the data packet (S5) and calculates a fundamental frequency of the voice signal by means of the sampling data contained in the data packet (S6). The sampling device sets a timer based on the fundamental frequency calculated by the calculating device and outputs a trigger signal upon expiration of the timer (S11).

11 Claims, 3 Drawing Sheets

(51) Int. Cl.
  *A61B 5/00* (2006.01)
  *A61B 7/00* (2006.01)
  *A61B 7/02* (2006.01)
  *A61B 7/04* (2006.01)
  *G10L 25/66* (2013.01)
  *G10L 25/90* (2013.01)

(52) U.S. Cl.
  CPC ............ *A61B 5/7285* (2013.01); *A61B 7/003* (2013.01); *A61B 7/023* (2013.01); *A61B 7/04* (2013.01); *G10L 25/66* (2013.01); *G10L 2025/906* (2013.01)

(56) References Cited

U.S. PATENT DOCUMENTS

| | | | |
|---|---|---|---|
| 4,241,729 A | 12/1980 | Aoshiro | |
| 4,404,963 A | 9/1983 | Kohri | |
| 4,670,009 A | 6/1987 | Bullock | |
| 5,245,133 A | 9/1993 | DeCarlo et al. | |
| 5,569,157 A | 10/1996 | Nakazawa et al. | |
| 5,588,950 A | 12/1996 | Sano | |
| 5,630,419 A | 5/1997 | Ranalletta | |
| 6,383,132 B1 | 5/2002 | Wimmer | |
| 6,547,722 B1 | 4/2003 | Higuma et al. | |
| 6,582,361 B2 | 6/2003 | Hirano | |
| 6,716,160 B2 | 4/2004 | Mitsumori | |
| 6,734,893 B1* | 5/2004 | Hess ................ A61B 1/2673 348/65 |
| 7,179,223 B2 | 2/2007 | Motoki et al. | |
| 7,198,599 B2 | 4/2007 | Goto et al. | |
| 7,841,880 B2 | 11/2010 | Ikeda | |
| 2001/0025135 A1 | 9/2001 | Naito et al. | |
| 2002/0040180 A1 | 4/2002 | Hirano | |
| 2002/0115907 A1 | 8/2002 | Mitsumori | |
| 2003/0092965 A1 | 5/2003 | Konomura | |
| 2004/0015050 A1 | 1/2004 | Goto et al. | |
| 2004/0143162 A1 | 7/2004 | Krattiger et al. | |
| 2005/0004434 A1 | 1/2005 | Bob et al. | |
| 2006/0074383 A1 | 4/2006 | Boulais | |
| 2006/0116550 A1 | 6/2006 | Noguchi | |
| 2006/0135851 A1 | 6/2006 | Yamazaki | |
| 2006/0199999 A1 | 9/2006 | Ikeda | |
| 2006/0252993 A1 | 11/2006 | Freed | |
| 2007/0106119 A1 | 5/2007 | Hirata et al. | |
| 2007/0156018 A1 | 7/2007 | Krauter et al. | |
| 2007/0221701 A1 | 9/2007 | Ortiz | |
| 2007/0282371 A1 | 12/2007 | Lee | |
| 2009/0180124 A1* | 7/2009 | Chen ................ G01H 9/002 356/496 |
| 2009/0209820 A1 | 8/2009 | Tanaka | |
| 2009/0281390 A1* | 11/2009 | Qiu ................ A61B 1/2673 600/199 |
| 2009/0286412 A1 | 11/2009 | Ikeda | |
| 2010/0168560 A1 | 7/2010 | Hauck et al. | |
| 2011/0082494 A1 | 4/2011 | Kerr et al. | |
| 2011/0288372 A1 | 11/2011 | Petersen | |
| 2011/0313252 A1 | 12/2011 | Lin | |
| 2012/0209068 A1 | 8/2012 | Hosaka | |
| 2014/0135576 A1 | 5/2014 | Hebert et al. | |
| 2014/0148646 A1 | 5/2014 | Inada | |
| 2015/0057537 A1 | 2/2015 | Dillon et al. | |
| 2015/0173711 A1 | 6/2015 | Hiraoka | |

FOREIGN PATENT DOCUMENTS

| | | |
|---|---|---|
| CN | 101730499 A | 6/2010 |
| CN | 102307510 A | 1/2012 |
| CN | 102401995 A | 4/2012 |
| CN | 102697445 A | 10/2012 |
| CN | 102753084 A | 10/2012 |
| CN | 202748535 U | 2/2013 |
| CN | 103153152 A | 6/2013 |
| CN | 103211566 A | 6/2013 |
| DE | 69 05 185 U | 4/1972 |
| DE | 34 46 698 A1 | 7/1985 |
| DE | 196 27 016 C1 | 2/1998 |
| DE | 101 48 099 B4 | 6/2006 |
| DE | 102010034623 | 2/2012 |
| DE | 10 2012 009332 | 11/2013 |
| EP | 0 028 396 B1 | 4/1981 |
| EP | 0055394 | 7/1982 |
| EP | 1420592 A1 | 5/2004 |
| EP | 1475031 | 11/2004 |
| EP | 1 759 626 A2 | 3/2007 |
| ES | S 2356497 | 4/2011 |
| JP | S 48 27116 | 8/1973 |
| JP | S 61 118713 | 6/1986 |
| JP | S 62 227312 | 10/1987 |
| JP | H 06254049 | 9/1994 |
| JP | 10-225439 | 8/1998 |
| JP | H 11244225 | 9/1999 |
| JP | A-2001-061772 | 3/2001 |
| JP | 2001510696 | 8/2001 |
| JP | 2002-160691 | 6/2002 |
| JP | 2002 291699 A | 10/2002 |
| JP | 2003 190085 | 7/2003 |
| JP | 2005 304 586 A | 11/2005 |
| JP | 3882088 B1 | 2/2007 |
| JP | 2007 111541 | 5/2007 |
| JP | 2007 252921 | 10/2007 |
| JP | 2007313047 | 12/2007 |
| JP | 2009 505688 | 2/2009 |
| JP | 2009 101134 | 5/2009 |
| JP | 2009 530051 | 8/2009 |
| JP | 2009 201762 | 9/2009 |
| JP | 2012 245058 | 12/2012 |
| WO | WO 00/13569 A1 | 3/2000 |
| WO | WO 00/33727 A1 | 6/2000 |
| WO | WO 2005/094665 | 10/2005 |
| WO | WO2008056642 A1 | 5/2008 |
| WO | WO 2009/008596 A1 | 1/2009 |
| WO | WO 2011/108157 | 9/2011 |
| WO | WO 2011/114772 A1 | 9/2011 |
| WO | WO 2013/129204 | 9/2013 |

OTHER PUBLICATIONS

Search Report for Application CN 2014800410593 in 2 pages (English translation).
Search Report for Application CN 201480076051 in 2 pages (English translation).
Office Action dated Sep. 4, 2017 in 7 pages for Chinese Application No. 201580005641.9 (English translation).
Oct. 8, 2014 Int'l Search Report from related PCT App. No. PCT/EP2014/065587 (4 pgs).
Jan. 13, 2015 Int'l Search Report from related PCT App. No. PCT/EP2014/073064 (4 pgs).
Jan. 19, 2015 Int'l Search Report from related PCT App. No. PCT/EP2014/073065 (6 pgs).
Mar. 2, 2015 Int'l Search Report from related PCT App. No. PCT/EP2014/077938 (3 pgs).
Mar. 24, 2015 Int'l Search Report from related PCT App. No. PCT/EP2014/075902 (4 pgs).
Mar. 24, 2015 Int'l Search Report from related PCT App. No. PCT/EP2015/051252 (4 pgs).
Jan. 13, 2015 Int'l Search Report from related PCT App. No. PCT/EP2014/073066 (4 pgs).
Anonymous: "Products I BMP-TAPPI", , Jun. 30, 2013 (Jun. 30, 2013), XP055394249, Gefunden im Internet: URL:https://web.archive.org/web/20130630082009/http :// www.bmp-tappi.com:80/products [gefunden am Jul. 27, 2017].
Anonymous: "10. Tappo per innesti rapidi femmina", , Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n nesti- rapidifemmina [gefunden am Jul. 27, 2017].
International Search Report dated Apr. 30, 2015 for International Application No. PCT/EP2015/051245 in 6 pages.

(56) References Cited

OTHER PUBLICATIONS

International Search Report for Application No. 2015800056423 in 2 pages dated Apr. 23, 2018.

* cited by examiner

TRACKING THE FUNDAMENTAL FREQUENCY OF A VOICE SIGNAL IN REAL TIME

The present invention relates to a tracking of a voice signal in real time.

A fundamental frequency analysis of the voice signal of a test person is required, for example, in the field of stroboscopy. By means of stroboscopy, the movability of the vocal folds can be judged. Triggering of an image acquisition of the vocal folds takes place, for example, by means of phonation of the test person via a body or air-conduction microphone.

For initiating phonation, the vocal folds are brought into a phonation position, which means that they loosely contact each other, thereby closing the glottis. Due to the air current, the vocal folds are made to vibrate, so that with each opening and closing, the air is intermittently released into the articulation space, which results in complicated periodic vibrations consisting of partials. The frequency, e.g. 70-1000 Hz, depends on the length of the vocal folds.

In the field of stroboscopy, a stroboscope is driven on the basis of this (fundamental) frequency. The stroboscope attached to an endoscope serves to acquire images of the vocal folds at suitable points in time which are determined by means of the fundamental frequency of the voice signal.

An object of the invention consists in simplifying a structure for tracking the fundamental frequency of a voice signal, for example, in spectroscopy.

This object is achieved by the method and the apparatus according to the attached claims.

In accordance with the invention, a sampling device samples a voice signal of a test person for a predetermined period of time, thus obtaining sampling data of the voice signal, forms a data packet from the sampling data, and sends the data packet to a calculating device. The calculating device receives the data packet and calculates a fundamental frequency of the voice signal by means of the sampling data contained in the data packet. The sampling device sets a timer on the basis of the fundamental frequency calculated by the calculating device and outputs a trigger signal upon expiration of the timer.

An advantage of the invention consists in that the recording of the voice signal and the analysis of the voice signal can be carried out at different locations, so that the structure of a recording apparatus can be reduced in size. Moreover, it is possible to determine the fundamental frequency of the voice signal asynchronously to the driving of a stroboscope; in this way, a complex structure for determining the fundamental frequency in real time can be avoided.

In the following, the invention is described in more detail by means of embodiments while referring to the attached drawings:

FIG. 1 shows flow charts for a process 1, a process 2, and a process 3 for tracking the fundamental frequency of a voice signal according to an embodiment of the invention.

Figure 1:
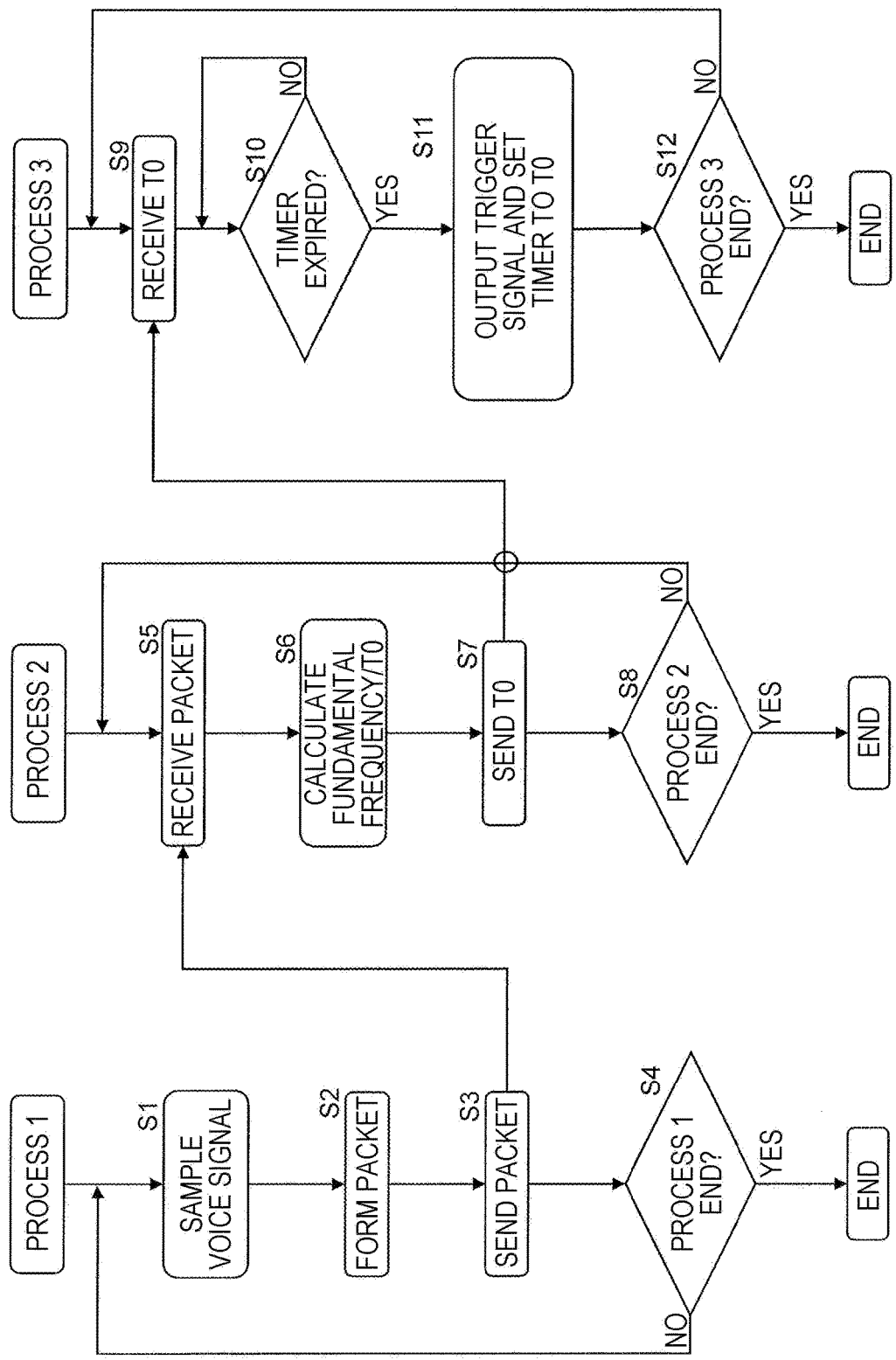

FIG. 1 illustrates three processes, namely process 1, process 2 and process 3, wherein processes 1 and 2 or 3 and 2 may respectively be implemented at different locations, and processes 1 and 3 may be implemented at the same location.

Process 1 comprises the following steps: Sampling (S1) a voice signal, for example, a phonation flow, of a test person for a predetermined period of time, thus obtaining sampling data of the voice signal, forming (S2) a data packet from the sampling data, sending (S3) the data packet to a calculating device, and repeating these steps as long as process 1 is not terminated (No in S4).

Process 2 comprises the following steps: Receiving (S5) the data packet from a sampling device, calculating (S6), by means of the sampling data contained in the data packet, a fundamental frequency f0 of the voice signal at the calculating device and calculating T0=1/f0, sending (S7) T0 to the sampling device, and repeating these steps as long as process 2 is not terminated (No in S8).

Process 3 comprises the following steps: Receiving (S9) T0 at the sampling device, checking (S10) whether a timer has expired, outputting a trigger signal and setting (S11) the timer to T0, when the timer has expired (Yes in S10), and repeating these steps as long as process 3 is not terminated (No in S11).

At the beginning of process 3, when T0 has not yet been received from process 2, the timer can be set to a predetermined value of T0. If the received value of T0 differs from the predetermined value of T0 or from the previously set value of T0, the timer, after it has expired, is set to the received value of T0. In other words, the timer is always set to the current value of T0.

The timer is preferably located on the side of the sampling device which collects the sampling data. Upon expiration of the timer, the trigger signal is output to a flash lamp or a stroboscope in order to generate a flash signal for acquiring, for example, an image of the vocal folds by means of a camera.

So as to avoid jumps between a value of T0 previously set in the timer and a value of T0 newly to be set in the timer, the transition between the old and the new value of T0 is, according to an embodiment of the invention, implemented smoothly, for example, by using a known loop controller.

The trigger signal output upon expiration of the timer can drive a stroboscope which is, for example, arranged close to the glottis of the test person and, together with a camera, serves to acquire an image of the glottis.

In step S1, the voice signal is recorded, for example, by means of a microphone which is arranged close to the glottis of the test person.

The data packet formed in step S2 contains a specified number of sampling values of the voice signal, the sampling values being acquired by the sampling of the voice signal for the predetermined period of time. For instance, the transition from step S1 to step S2 can be triggered when the specified number of the sampling values has been acquired. In other words, the formation of the data packet is triggered when the specified number of the sampling values has been acquired.

Figure 2:
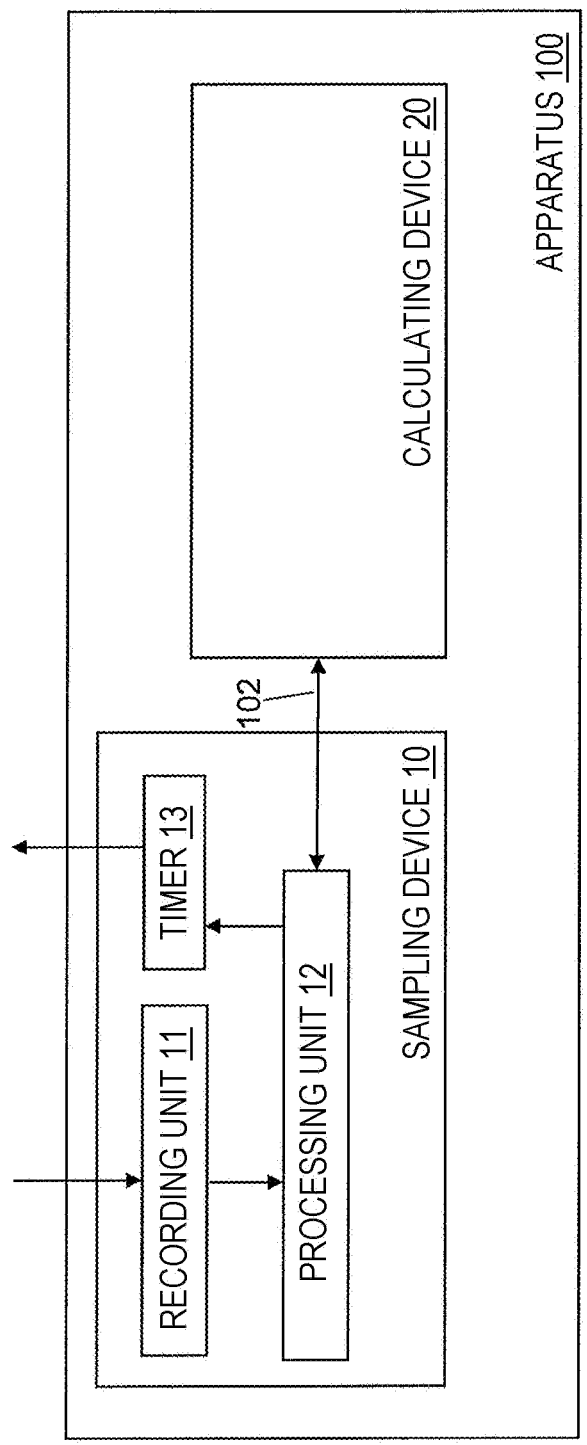
FIG. 2 shows a schematic block diagram of an apparatus for tracking the fundamental frequency of a voice signal according to an embodiment of the invention.

FIG. 2 shows a schematic block diagram of an apparatus 100 for tracking the fundamental frequency of a voice signal according to an embodiment of the invention.

The apparatus 100 comprises a sampling device 10 and a calculating device 20. The processes 1 and 3 described above can be implemented in the sampling device 10 which is, for example, attached to an endoscope. The process 2 can be implemented in the calculating device 20 which is provided separately.

The sampling device 10 comprises a recording unit 11, a processing unit 12 and a timer 13. The recording unit 11 receives the voice signal recorded by the microphone. The microphone can be comprised by the recording unit 11.

The processing unit 12 receives the recorded voice signal from the recording unit 11 and carries out sampling of the voice signal at a specified sampling frequency. In doing so, sampling values having a specified resolution in bits are obtained. The processing unit 12 joins the sampling values together into data packets having a specified bit length. In other words, a data packet contains a specified number of data values. When a specified number of data values has been obtained by the sampling, the processing unit 12 generates the data packet and sends it to the calculating device 20. The functions of the processing unit 12 can be implemented by a DSP (Digital Signal Processor), an FPGA (Field Programmable Gate Array) or the like. The processing unit 12 can also comprise a processor and a memory that stores a program which, when being executed by the processor, realizes the above described functions of the processing unit 12.

The data packets can be sent to the calculating device 20 via a serial interface 102. The connection between sampling device 10 and calculating device 20 can be wired or wireless.

The calculating device 20 receives the data packet from the sampling device 10 and, by means of the sampling values contained therein, calculates the fundamental frequency f0 of the voice signal. In other words, the calculating device 20 carries out a frequency analysis of the voice signal by means of the sampling values contained in the data packet. The calculating device 20 also calculates a time $T0=1/f0$. The calculating device 20 sends T0 to the sampling device 10, for example, via the serial interface 102.

The functions of the calculating device 20 can be implemented by a DSP (Digital Signal Processor), an FPGA (Field Programmable Gate Array) or the like. The calculating device 20 can also comprise a processor and a memory that stores a program which, when being executed by the processor, realizes the above described functions of the calculating device 20.

The time T0 sent by the calculating device 20 is supplied to the timer 13, for example, via the processing unit 12. The timer 13 is set to T0, and upon expiration of the time T0, a trigger signal is output, for example, for driving a flash lamp or a stroboscope.

Figure 3:
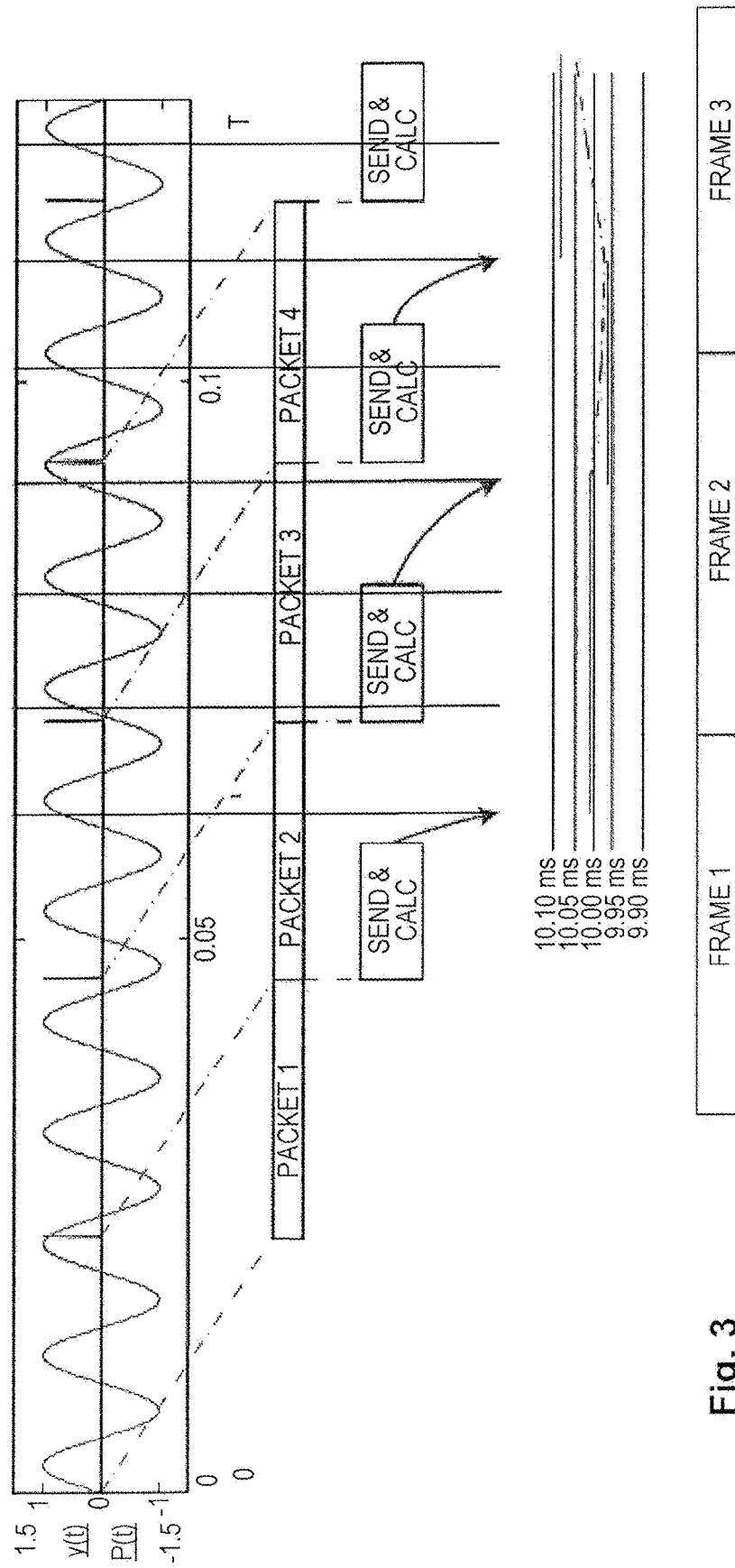
FIG. 3 shows a schematic representation of a tracking of the fundamental frequency of a voice signal according to an embodiment of the invention.

FIG. 3 shows a representation which illustrates the detection and tracking of a fundamental frequency f0 of a voice signal according to an embodiment of the invention.

y(t) represents a signal curve of a voice signal of a test person. FIG. 3 shows the signal curve as a sinusoidal wave having a frequency of 100 Hz. For instance, the recording unit 11 can provide the signal curve y(t) for the processing unit 12.

The sampling rate at which the signal curve is sampled amounts to 44.1 kHz, which corresponds to a time duration of approximately 22.7 μs. The resolution of a sampling value amounts to 16 bits and the packet length comprises 1023 bytes, which corresponds to a time duration of approximately 23.22 ms. It is noted that the invention is not restricted to these values. A data packet can, for example, contain ten oscillations of the voice signal.

If sampling values of 1024 bytes have been obtained, a trigger signal P(t) triggers the generation or the completion and the sending of the data packet. FIG. 3 shows data packets, namely Packet 1, Packet 2, Packet 3 and Packet 4, whose generation and sending are triggered by P(t).

The above described sampling of the signal curve y(t) and the generation and the sending of the data packets can be carried out in process 1 shown in FIG. 1 and by the sampling device 10 in FIG. 2, respectively.

By means of the sampling values contained in the data packets, the fundamental frequency f0 of the signal curve y(t) is calculated. f0 is, for the first time, calculated by means of the data packet (Packet 1). FIG. 3 illustrates the delay between signal curve sampling, packet generation, sending the packet, calculating of f0 and T0, and setting the timer to T0.

When calculating f0 for the first time, the timer is set to $T0=1/f0$. If f0 has changed after the processing of the data packet (Packet 2), the timer, after the previously set time has expired, is set to the newly calculated time, or the old value of T0 and the new value of T0 can be averaged. It is also possible to add a constant phase or a phase increasing with time to T0, in order to enable a smooth transition between the old value and the new value of T0.

By means of the above described configuration, the fundamental frequency f0 can be tracked over time. In particular, based on the operation of the processing of the data packets, which is asynchronous to the voice signal, again a real time trigger signal, which is synchronous to the voice signal, is generated for the flash lamp or the stroboscope.

For instance, a stroboscope is attached to an endoscope which is provided close to the glottis of the test person. By means of the trigger signal, the stroboscope generates a light flash, and a camera attached to the endoscope acquires an image of the vocal folds. FIG. 3 illustrates the acquired images as asynchronous image data packets Frame 1, Frame 2, Frame 3.

The above described calculation of the fundamental frequency f0 can be carried out in process 2 shown in FIG. 1 or by the calculating device 20 in FIG. 2. The generation of the trigger signal can be carried out by process 3 or by the sampling device 10, in particular by setting the timer 13.

The delay between the first sampling for a data packet and the driving at the (newly) calculated fundamental frequency f0 amounts to approximately 61.64 ms in the example shown in FIG. 3; however, this is negligible for the acquisition of suitable images of the vocal folds.

In accordance with the invention, sampling data obtained by sampling a voice signal are sent in data packets to a device where they are processed for detecting the fundamental frequency of the voice signal. In this way, the structure at the sampling device can be reduced in size. Moreover, it is possible to determine the fundamental frequency of the voice signal asynchronously to the actuation of a stroboscope, whereby a complex structure for determining the fundamental frequency in real time can be avoided.

The invention claimed is:
1. A method comprising:
 (a) sampling, via a sampling device, a voice signal of a test person for a predetermined period of time, thus obtaining sampling data of the voice signal, wherein the predetermined period of time comprises a specified number of oscillations of the voice signal, and triggering process (b) when a specified number of sampling values has been acquired by the sampling of the voice signal for the predetermined period of time, wherein the sampling device is attached to an endoscope and the sampling device includes a first processor, a first one or more data stores configured to store a first set of computer-executable instructions, and a microphone that is configured to record the voice signal of the test person;

(b) forming, via the sampling device, a data packet from the sampling data, wherein the data packet includes the specified number of sampling values of the voice signal;
(c) sending, via a serial interface by the sampling device, the data packet from the sampling device to a calculating device;
(d) calculating, via the calculating device, from the sampling data contained in the data packet, a fundamental frequency of the voice signal and sending the fundamental frequency to the sampling device via the serial interface, wherein the calculating device includes a second processor and a second one or more data stores configured to store a second set of computer-executable instructions;
(e) setting and initiating, via the sampling device, a timer with a duration that is based at least in part on the fundamental frequency, wherein initiating the timer includes allowing the timer run till expiration of the duration; and
(f) outputting, via the sampling device, a trigger signal upon expiration of the timer, wherein processes (a), (b), (c), and (d) are repeated a specified number of times, process (e) is repeated after expiration of the duration, processes (a), (b), (c), (e), and (f) are performed by the first processor by executing the first set of computer-executable instructions, and process (d) is performed by the second processor by executing the second set of computer-executable instructions.

2. The method according to claim 1, further comprising: outputting the trigger signal to a stroboscope which is arranged close to a glottis of the test person.

3. The method according to claim 1, wherein the voice signal is a phonation flow.

4. An apparatus comprising:
a sampling device attached to an endoscope, wherein the sampling device includes:
 a first processor,
 a first one or more data stores configured to store a first computer-executable instructions, and
 a microphone configured to record a voice signal of a test person;
a calculating device, wherein the calculating device includes:
 a second processor, and
 a second one or more data stores configured to store a second computer-executable instructions;
a serial interface electronically connecting the calculating device and the sampling device together;
wherein the first computer-executable instructions, when executed by the first processor, configure the first processor to:
 (a) sample, via the sampling device, the voice signal of the test person for a predetermined period of time, thus obtaining sampling data of the voice signal, wherein the predetermined period of time comprises a specified number of oscillations of the voice signal;
 (b) in response to a specified number of sampling values having been acquired by the sampling of the voice signal for the predetermined period of time, form, via the sampling device, a data packet from the sampling data, wherein the data packet includes the specified number of sampling values of the voice signal; and
 (c) send, via a serial interface and by the sampling device, the data packet to the calculating device, wherein the calculating device is adapted to receive the data packet via the serial interface;
wherein the second computer-executable instructions, when executed by the second processor, configure the second processor to:
 (d) calculate, via the calculating device, a fundamental frequency of the voice signal from the sampling data contained in the data packet, and send the fundamental frequency to the sampling device via the serial interface; and
wherein the first computer-executable instructions, when executed by the first processor, further configure the first processor to:
 (e) set and initiate, via the sampling device, a timer with a duration that is based at least in part on the fundamental frequency wherein initiating the timer includes allowing the timer run till expiration of the duration; and
 (f) output, via the sampling device, a trigger signal upon expiration of the duration.

5. The apparatus according to claim 4, wherein the sampling device is adapted to output the trigger signal to a stroboscope attached to the endoscope.

6. The apparatus according to claim 4, wherein the first processor is further configured to:
output the trigger signal to a stroboscope which is arranged close to a glottis of the test person.

7. The apparatus according to claim 4, wherein the voice signal is a phonation flow.

8. A method comprising:
(a) sampling, via a sampling device, a voice signal of a test person for a predetermined period of time, thus obtaining sampling data of the voice signal, wherein the predetermined period of time comprises a specified number of oscillations of the voice signal, and triggering process (b) when a specified number of sampling values has been acquired by the sampling of the voice signal for the predetermined period of time, wherein the sampling device is attached to an endoscope and the sampling device includes a first processor, a first one or more data stores configured to store a first set of computer-executable instructions, and a microphone that is configured to record the voice signal of the test person;
(b) forming a data packet from the sampling data, wherein the data packet includes the specified number of sampling values of the voice signal;
(c) sending, via a serial interface, the data packet from the sampling device to a calculating device;
(d) receiving, from the calculating device via the serial interface, a fundamental frequency of the voice signal;
(e) setting and initiating a timer with a duration that is based at least in part on the fundamental frequency, wherein initiating the timer includes allowing the timer run till expiration of the duration; and
(f) outputting a trigger signal upon expiration of the timer, wherein processes (a), (b), (c), and (d) are repeated a specified number of times, process (e) is repeated after expiration of the duration, process (d) is performed asynchronously to processes (a), (b), (c), (e), and (f).

9. The method according to claim 8, wherein the sampling device is adapted to output the trigger signal to a stroboscope attached to the endoscope.

10. The method according to claim 8, further comprising: outputting the trigger signal to a stroboscope which is arranged close to a glottis of the test person.

11. The method according to claim 8, wherein the voice signal is a phonation flow.

\* \* \* \* \*